United States Patent
Habibabadi et al.

(10) Patent No.: US 12,073,947 B1
(45) Date of Patent: Aug. 27, 2024

(54) META-LEARNING FOR AUTOMATED HEALTH SCORING

(71) Applicant: INTUIT INC., Mountain View, CA (US)

(72) Inventors: Nazanin Zaker Habibabadi, Sunnyvale, CA (US); Makanjuola Adekunmi Ogunleye, Blacksburg, VA (US); Jeremy S. Krohn, Reno, NV (US); Xue Han, Sunnyvale, CA (US)

(73) Assignee: INTUIT INC., Mountain View, CA (US)

( * ) Notice: Subject to any disclaimer, the term of this patent is extended or adjusted under 35 U.S.C. 154(b) by 0 days.

(21) Appl. No.: 18/190,529

(22) Filed: Mar. 27, 2023

(51) Int. Cl.
| | |
|---|---|
| *G06Q 30/02* | (2023.01) |
| *G06N 5/022* | (2023.01) |
| *G06Q 10/06* | (2023.01) |
| *G06Q 10/10* | (2023.01) |
| *G06Q 30/0282* | (2023.01) |
| *G06Q 30/06* | (2023.01) |
| *G16H 50/30* | (2018.01) |

(52) U.S. Cl.
CPC ............ *G16H 50/30* (2018.01); *G06N 5/022* (2013.01); *G06Q 30/0282* (2013.01)

(58) Field of Classification Search
CPC ..... G16H 50/30; G06N 5/022; G06Q 30/0282
USPC ................................................. 705/1.1–912
See application file for complete search history.

(56) References Cited

U.S. PATENT DOCUMENTS

| | | | | |
|---|---|---|---|---|
| 10,275,838 B2 * | 4/2019 | DeLuca | ................ | H04L 67/306 |
| 11,263,523 B1 * | 3/2022 | Duchon | ................ | G06N 3/088 |
| 2010/0275128 A1 * | 10/2010 | Ward | ................ | G06Q 10/10 |
| | | | | 715/744 |
| 2012/0209918 A1 * | 8/2012 | Shah | ................ | G06Q 30/0251 |
| | | | | 709/205 |
| 2013/0138577 A1 * | 5/2013 | Sisk | ................ | G06Q 40/04 |
| | | | | 705/36 R |
| 2019/0066115 A1 * | 2/2019 | Harris | ................ | G06Q 10/06395 |
| 2019/0171438 A1 * | 6/2019 | Franchitti | ................ | G06N 3/08 |
| 2021/0201394 A1 * | 7/2021 | Lemanski | ................ | G06Q 40/02 |
| 2022/0083615 A1 * | 3/2022 | Alamuri | ................ | G06F 16/9535 |

(Continued)

OTHER PUBLICATIONS

Zhou, J., Cui, H., Li, X., Yang, W., & Wu, X.. "A novel phishing website detection model based on LightGBM and domain name features." Symmetry, 15(1), 180. Jan. 7, 2023. (Year: 2023).*

*Primary Examiner* — Jonathan P Ouellette
(74) *Attorney, Agent, or Firm* — Patterson + Sheridan, LLP

(57) ABSTRACT

Aspects of the present disclosure provide techniques for automated health scoring through meta-learning. Embodiments include retrieving text data related to an entity that was provided by a user and providing one or more first inputs to a first machine learning model based on a subset of the text data. Embodiments include determining, based on an output from the first machine learning model, whether the text data includes an address. Embodiments include determining that the text data includes a name and determining, based on the address and the name, that one or more text results from one or more data sources relate to the entity. Embodiments include providing one or more second inputs to a second machine learning model based on the one or more text results and determining, based on an output from the second machine learning model, a health score for the entity.

19 Claims, 6 Drawing Sheets

(56) References Cited

U.S. PATENT DOCUMENTS

2023/0134796 A1\* 5/2023 Bhatnagar ............ G06F 40/295
704/9

\* cited by examiner

META-LEARNING FOR AUTOMATED HEALTH SCORING

INTRODUCTION

Aspects of the present disclosure relate to techniques for using meta-learning for automated health scoring. In particular, embodiments involve automated feature identification and extraction for entities as well as the use of a combination of machine learning technologies in a particular manner to evaluate the health of the entities based on such features.

BACKGROUND

Every year millions of people, businesses, and organizations around the world utilize software applications to assist with countless aspects of life. Commerce in particular has been significantly impacted by advances in computing technology. Many software applications provide various commercial services, such as performing financial management and allowing users to conveniently buy and sell products and services.

Some software applications provide automated services for providing users with targeted content, such as offers, promotions, recommendations, advertisements, fraud alerts, and other types of content. Such automated services may be based on automated determinations about attributes of particular entities, such as whether a business is "healthy" according to a variety of health indicators. For example, some software applications may determine a health score for an entity indicating an extent to which the entity exhibits favorable and/or unfavorable traits across a variety of relevant categories. However, existing techniques for automated health scoring are limited by the data points known to be associated with an entity, and it can be challenging to locate and utilize data about an entity with any degree of confidence. In many cases, a software application may not have access to enough data that is known to be associated with a given entity to accurately determine a health score for the given entity. Furthermore, existing techniques may rely on isolated data that provides only a limited view of the overall health of an entity, thus resulting in inaccurate or misleading automated determinations.

What is needed are improved techniques for automated health scoring that make better use of available electronic data in order to provide a more accurate and holistic representation of the health of entity for improved automated determinations.

BRIEF SUMMARY

Certain embodiments provide a method for automated health scoring through meta-learning. The method generally includes: retrieving text data related to an entity that was provided by a user; providing one or more first inputs to a first machine learning model based on a subset of the text data; determining, based on an output from the first machine learning model in response to the one or more first inputs, whether the text data includes an address; determining that the text data includes a name; determining, based on the address and the name, that one or more text results from one or more data sources relate to the entity; providing one or more second inputs to a second machine learning model based on the one or more text results; determining, based on an output from the second machine learning model in response to the one or more second inputs, a health score for the entity; and performing one or more actions based on the health score for the entity.

Other embodiments comprise systems configured to perform the method set forth above as well as non-transitory computer-readable storage mediums comprising instructions for performing the method set forth above.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
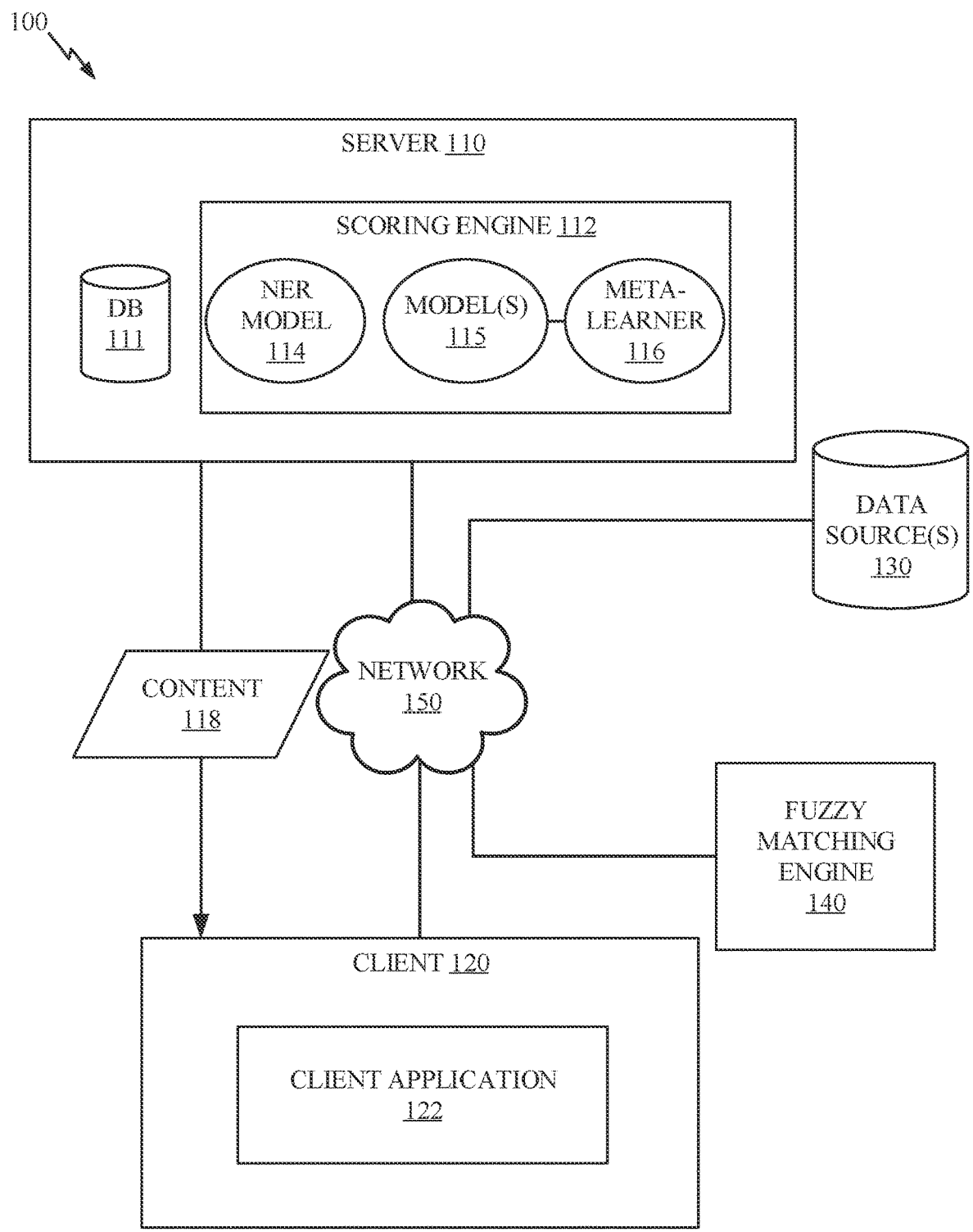
FIG. 1 depicts example components related to automated health scoring through meta-learning.

Aspects of the present disclosure provide apparatuses, methods, processing systems, and computer-readable mediums for automated health scoring through meta-learning.

Embodiments described herein involve automatically locating and identifying text results that are related to an entity, such as online reviews related to a business, through a process involving machine learning, fuzzy matching, and/or vector representations (e.g., embeddings). An entity may be a business, group, individual, and/or the like. In one example, text results related to an entity are retrieved from publicly available data sources and processed using particular machine learning and automated matching techniques in order to confirm whether the text results correspond to the entity. Text results that are confirmed to correspond to the entity are then used as part of a process by which features of the entity are generated and provided as inputs to a meta-learner, which may be an ensemble of machine learning models, in order to determine a health score for the entity. The health score for the entity determined using the meta-learner may then be used to make one or more automated determinations, such as whether to provide content related to the entity to one or more users, whether to provide content, products, and/or services to the entity itself, whether to proceed with a particular business decision, whether to generate a fraud alert, to assess risk, and/or the like. Furthermore, in some embodiments, the health score for the entity determined using the meta-learner may be provided to one or more endpoints, such as to be displayed to a user and/or used in one or more other processes.

Information used to identify matching text results (e.g., from online sources) for an entity may come from user-provided data relating to the entity. For example, a user representing a business may enter information about the business, such as when configuring a profile with a software application that performs certain operations described herein related to automated health scoring. The user-provided information is stored in association with the software application, such as in a database. In some cases, users may enter imprecise, incomplete, poorly formatted, or otherwise problematic information, and it may be challenging to match text results (e.g., online reviews) to the entity based on such information.

According to certain embodiments, user-provided information about an entity may be discarded without further processing unless it is determined to contain both an address (e.g., a physical address) and a name of an entity, thus avoiding utilizing data that is unlikely to be helpful for locating text results associated with an entity. For example, as described in more detail below with respect to FIGS. 1 and 2, a name entity recognition (NER) model may be trained using supervised machine learning techniques based on a training data set to determine whether a given text input (e.g., from user-provided data, such as in an address field) includes an address and, if so, such an address may be extracted from the given text input. For example, the NER model may be trained to identify addresses in text. In some embodiments, extraneous characters, spacing, incorrect formatting, and/or the like may be corrected in pre-processing before text is provided to the NER model (e.g., to place the address in a correct form even if it was not correctly entered by the user), and the NER model may output an indication of whether the pre-preprocessed text contains an address and therefore can be extracted as the address. If the user-provided data for the entity includes an address of the entity, the user-provided data may also be analyzed to determine whether it includes a name of the entity (e.g., in a different field of the user-provided data, such as a name field). If a name has been provided and an address was also successfully extracted using the NER model, then the name and address may be used to locate text results from one or more data sources, such as websites from which reviews can be retrieved.

In one example, the name and address are provided to an application programming interface (API) associated with one or more data sources in order to retrieve text results from the one or more data sources that may be matched to the entity. In some embodiments, the one or more data sources may utilize fuzzy matching (e.g., in response to the API request) to locate relevant text results. Certain embodiments further involve confirming matches that are returned from the one or more data sources, such as based on comparison of embeddings. An embedding generally refers to a vector representation of an item (e.g., text such as a word or string) that represents the item as a vector in n-dimensional space such that similar items (e.g., words or strings with similar meanings) are represented by vectors that are close to one another in the n-dimensional space. A text result that is returned as a match from a data source (e.g., based on fuzzy matching) and/or that has been validated (e.g., through a comparison of embeddings) may be confirmed to be a match for the entity, and may be used in further processing associated with determining an automated health score for the entity.

As described in more detail below with respect to FIG. 3, a meta-learner may be an ensemble of machine learning models that is trained to output a health score for an entity based on a variety of different types of input features related to the entity. For example, text results that are confirmed to be associated with an entity, as well as other data known to be related to the entity, may be used to provide inputs to one or more machine learning models of the meta-learner in order to determine the health score. The machine learning models may include, for example, one or more sentiment models that are trained to output sentiment scores and/or tags indicating sentiments present in text results (e.g., positive or negative sentiments), one or more machine learning models that determine trends that are indicated by an ordered series of text results (e.g., business reviews that trend more positive over time), one or more machine learning models trained to summarize text results and/or generate embeddings of the text results and/or summaries, as well as other types of machine learning models. The meta-learner may utilize outputs from a plurality of individual models in the ensemble to determine a health score for an entity represented by the input data, such as a numerical (e.g., decimal) value between 0 and 1 that indicates an overall health of the entity.

As described in more detail below with respect to FIG. 4, health scores determined using techniques described herein may be used for a variety of different useful purposes, such as fraud detection, risk assessment, providing targeted content via a software application, and/or the like. For example, a health score for an entity may be used to determine whether to provide an alert to a potential customer of the entity, whether to recommend a particular entity to a potential customer or to another entity, whether to provide a discount, offer, or service to the entity, whether to provide content related to the entity to one or more users, and/or the like.

In some embodiments, the various machine learning models described herein may be continuously improved over time based on user feedback. For example, user feedback with respect to a health score determined using the meta-learner (e.g., indicating whether the health score is accurate) may be used to re-train the meta-learner, including the various machine learning models that may be included therein, for improved future performance. Thus, as a result of such a feedback loop by which the meta-learner is iteratively improved, subsequent health score determinations made using the meta-learner may be more accurate.

Techniques described herein improve the technical fields of automated health scoring and related automated determinations by software applications in a number of ways. For instance, by automatically locating and matching text results to an entity based on the use of machine learning techniques to extract an address and name of the entity from user-provided data, embodiments of the present disclosure allow relevant and accurate data about an entity to be automatically identified in an accurate manner and used for improved automated health scoring in a manner that was not possible with conventional techniques. Techniques described herein allow up-to-date information, such as from online sources, to be identified and used in real-time or near-real-time to improve automated health scoring. Furthermore, by discarding user-provided data that is determined not to include an address or name of an entity based on machine learning, and discarding text results that are determined not to be a match for the entity, such as based on fuzzy matching and/or embeddings, techniques described herein avoid unnecessary processing and data storage associated with weakly or improperly matched electronic data, thereby improving the functioning of the computing devices involved and reducing inaccurate results.

Additionally, by utilizing a meta-learner that includes a variety of different machine learning models trained to output different types of useful data about an entity based on matched text results for the entity for use in determining a health score for the entity, techniques described herein improve the automated health scoring process by producing a result that more accurately reflects an overall health of the entity based on available electronic data. For example, while existing automated techniques may determine a health score based only on the limited data known through such existing techniques to be associated with an entity, thus producing a health score that may be inaccurate or misleading, techniques described herein overcome these deficiencies in existing automated techniques in order to produce a health score that is more indicative of the holistic health of an entity. As such, health scores determined using improved automated techniques described herein may be used for improved automated determinations by software applications, such as providing more accurate or relevant targeted content to users and/or making more accurate risk and/or fraud determinations. For example, by automatically selecting content, offers of products or services, and/or the like to provide to a user based on improved health scores determined using techniques described herein, a software application may avoid unnecessary processing and/or poor results associated with providing content and/or offers to users that are based on isolated, inaccurate, and/or misleading data.

Example Computing Components for Automated Health Scoring Through Meta-Learning

FIG. 1 is an illustration 100 of example computing components related to automated health scoring through meta-learning.

Illustration 100 includes a server 110, which comprises a scoring engine 112, which generally performs operations related to automated health scoring through meta-learning for use in automated determinations such as selecting content 118 to provide via a network 150 to a client 120 via a client application 122. Server 110 also includes a database (DB) 111, which stores entity data provided by users, such as when configuring profiles with a software application associated with scoring engine 112. In one example, DB 111 stores information entered by users that represent businesses, and the information may include addresses and names of businesses.

Server 110 may be a computing device such as system 600A of FIG. 6A, which is described in more detail below. Scoring engine 112 generally represents a software component that utilizes a name entity recognition (NER) model 114 and, in some embodiments, one or more additional models 115, which may be components of a meta-learner 116, in order to automatically determine a health score for an entity. It is noted that while NER model 114, model(s) 115, and meta-learner 116 are depicted within scoring engine 112, one or more of these models may alternatively be located outside of scoring engine 112 and/or outside of server 110, such as on one or more endpoints accessible by scoring engine 112 (e.g., via network 150).

There are many different types of machine learning models that can be used in embodiments of the present disclosure, such as for NER model 114, model(s) 115, and/or meta-learner 116. For example, one or more of these models may be a neural network. One or more of these models (e.g., meta-learner 116) may also be an ensemble of several different individual machine learning models. Such an ensemble may be homogenous (i.e., using multiple member models of the same type) or non-homogenous (i.e., using multiple member models of different types). Individual machine learning models within such an ensemble may all be trained using the same subset of training data or may be trained using overlapping or non-overlapping subsets randomly selected from the training data, and/or may be trained for different purposes and/or using different techniques. In one example, an ensemble including multiple different types of models that perform differing functions is trained together through a unified training process, such as based on outputs produced by a final layer of the ensemble.

Neural networks, for example, generally include a collection of connected units or nodes called artificial neurons. The operation of neural networks can be modeled as an iterative process. Each node has a particular value associated with it. In each iteration, each node updates its value based upon the values of the other nodes, the update operation typically consisting of a matrix-vector multiplication. The update algorithm reflects the influences on each node of the other nodes in the network. In some cases, a neural network comprises one or more aggregation layers, such as a softmax layer.

In some embodiments, training of a machine learning model is a supervised learning process that involves providing training inputs (e.g., representing text strings, representing entities, and/or the like) as inputs to a machine learning model. The machine learning model processes the training inputs and outputs predictions (e.g., indications of whether text strings contain addresses, indications of health scores for entities, and/or the like) based on the training inputs. The predictions are compared to the known labels associated with the training inputs (e.g., labels manually applied to training data by experts) to determine the accuracy of the machine learning model, and parameters of the machine learning model are iteratively adjusted until one or more conditions are met. For instance, the one or more conditions may relate to an objective function (e.g., a cost function or loss function) for optimizing one or more variables (e.g., model accuracy). In some embodiments, the conditions may relate to whether the predictions produced by the machine learning model based on the training inputs match the known labels associated with the training inputs or whether a measure of error between training iterations is not decreasing or not decreasing more than a threshold amount. The conditions may also include whether a training iteration limit has been reached. Parameters adjusted during training may include, for example, hyperparameters, values related to numbers of iterations, weights, functions used by nodes to calculate scores, and the like. In some embodiments, validation and testing are also performed for a machine learning model, such as based on validation data and test data, as is known in the art.

NER model 114 generally represents a machine learning model that is trained to output an indication of whether text input to the machine learning model contains an address, such as a physical address of an entity. In one example implementation, NER model 114 is built based on a Bidirectional Encoder Representations from Transformers (BERT) model, which involves the use of masked language modeling to determine text embeddings. In one embodiment, NER model 114 contains such a BERT model (or, more generally, an embedding model of some sort), and uses the BERT model to generate embeddings of input text for use in determining whether the input text includes an address. The BERT model may, for example, be pre-trained before being used to generate NER model 114, and may be further trained as part of the training of NER model 114 based on training data specific to the intended purpose of NER model 114 (e.g. address extraction). For instance, training inputs representing text results may be provided to NER model 114, and outputs produced by NER model 114 in response to the training inputs (e.g., indicating whether the text results include addresses) may be compared to known labels associated with the training inputs (e.g., based on user-provided labels indicating whether the text results represented in the training inputs include addresses). Parameters of NER model 114, including parameters of the BERT model or other type of embedding model, may be iteratively adjusted based on the comparing such that the BERT model is optimized along with the rest of NER model 114 for accuracy of the final output of NER model 114. It is noted that a BERT model is included as an example, and other types of machine learning models may also be used. In one example, NER model 114 includes an embedding model such as a BERT model as well as one or more additional layers, such as fully-connected layers and/or aggregation layers.

Meta-learner 116 generally represents an ensemble that includes one or more machine learning models 115. As described in more detail below with respect to FIG. 3, model(s) 115 may include one or more sentiment models (e.g., models trained to identify sentiments associated with text data, such as natural language text), one or more models trained to identify trends in series of input texts, one or more summarizer and/or vectorizer models (e.g., models trained to generate summaries of text and/or vector representations of text), and/or the like. In certain embodiments, model(s) 115 include one or more BERT models, one or more regression models, and/or the like. Meta-learner 116 may include model(s) 115, and may be trained to output a health score for an entity based on outputs from model(s) 115 in response to inputs to model(s) 115 (e.g., inputs that are based on text results matched to the entity by scoring engine 112 and, in some embodiments, based on one or more additional inputs related to the entity). Meta-learner 116 may use a variety of techniques to ensemble the results of model(s) 115, such as using outputs from model(s) 115 and/or additional data points as inputs to one or more layers or models that process such inputs and output a health score. In some embodiments, meta-learner 116 is trained in a holistic manner such that all of model(s) 115 and additional parameters of meta-learner 116 are trained together based on a set of training data (e.g., including features of an entity, such as including text results related to the entity, associated with labels indicating whether the entity is healthy or unhealthy). For example, while one or more of model(s) 115 may be pre-trained before being used as part of meta-learner 116, model(s) 115 may be further trained based on comparing ultimate outputs of meta-learner 116 with labels in the training data such that model(s) 115 are fine-tuned for accuracy of meta-learner 116. In one example, meta-learner 116 is a classifier model that outputs a numerical value (e.g., between 0 and 1) indicating a likelihood that an entity represented by input values is classified as healthy, and the numerical value is a used as a health score for the entity.

Data source(s) 130 generally represent endpoints that are accessible by scoring engine 112, such as via network 150, and that include data related to entities for which scoring engine 112 is used to generate health scores. For example, data source(s) 130 may include websites, databases, online accounts, and other endpoints from which data (e.g., text results) related to an entity may be retrieved. In one example, data source(s) 130 includes publicly available data sources that can be searched in order to locate and retrieve text results (e.g., online reviews) related to an entity (e.g., a business).

Fuzzy matching engine 140 generally represents a software component that is accessible by scoring engine 112, such as via network 150, and that performs "fuzzy matching" (e.g., matching that does not strictly require two items to be identical, such as matching that is based on various factors and/or thresholds, which may involve rules and/or machine learning) between two text strings, such as two identify text results in data source(s) 130 that are a match for a business. In one example, fuzzy matching engine 140 is a third-party tool, such as accessible via an application programming interface (API), that accepts text data as an input (e.g., the name and address of a business) and returns one or more text results (e.g., from data source(s) 130) that match the input text data according to fuzzy matching logic. In some embodiments, fuzzy matching engine 140 utilizes one or more machine learning models and/or rules as part of its matching logic. Fuzzy matching engine 140 may be used by scoring engine 112, such as in conjunction with one or more other techniques, to determine whether a text result retrieved from data source(s) 130 is a match for an entity.

For example, as described in more detail below with respect to FIG. 2, scoring engine 112 may retrieve entity data (e.g., provided by one or more users) for an entity from DB 111. Scoring engine 112 uses NER model 114 to determine whether the entity data retrieved from DB 111 contains an address (e.g., an actual physical address in text entered into an address field by the user) and, if so, extract the address in a proper format. Furthermore, if the entity data contains an address, scoring engine 112 determines whether the entity data contains a name of the entity (e.g., text entered into a name field by the user). If the entity data includes an address and a name, the name and address are used to retrieve one or more text results from data source(s) 130, such as based on one or more search terms and/or requests to an application programming interface (API), such as through communication with fuzzy matching engine 140. In one example, the entity is a business, and the text results are online reviews potentially related to the business retrieved from one or more locations accessible via the Internet. Text results that are determined by fuzzy matching engine 140 to be a match for the entity and that are returned to scoring engine 112 may, in some embodiments, be verified by scoring engine 112 as matches through an embedding comparison. For example, an embedding of the name from the entity data may be compared to an embedding of the name associated with the returned text result in order to determine whether the embeddings are within a threshold distance of each other. If the embedding comparison is successful, the text result may be determined to be a matching text result for the entity. As described in more detail below with respect to FIG. 3, scoring engine 112 then uses meta-learner 116, including model(s) 115, to determine a health score for the entity based at least in part on one or more matching text results for the entity.

The health score determined using techniques described herein may then be used to perform one or more actions, such as displaying the health score to the user, providing targeted content to a user, performing a risk assessment, fraud detection, determining whether to offer one or more products and/or services to the entity, and/or the like. In one example, server 110 selects content 118 to provide to a client 120, such as via client application 122, based on the health score. Client 120 may be a computing device such as system 600B of FIG. 6B, described in more detail below. For instance, as described in more detail below with respect to FIG. 4, content 118 may be an alert indicating that a business may be fraudulent or otherwise disreputable, such as based on a low health score being determined for the business using techniques described herein. In another example, content 118 is an offer of a loan, line of credit, or other financial product, and the determination to provide the offer and/or the terms of the offer may be based on the health score. Thus, techniques described herein may prevent fraud and/or otherwise improve targeting of content to users of software applications, while also avoiding utilizing physical computing resources that would otherwise be used in association with providing irrelevant or incorrect content to users based on inaccurate or misleading health scores determined using conventional techniques.

Example Text Matching for Automated Health Scoring Through Meta-Learning

Figure 2:
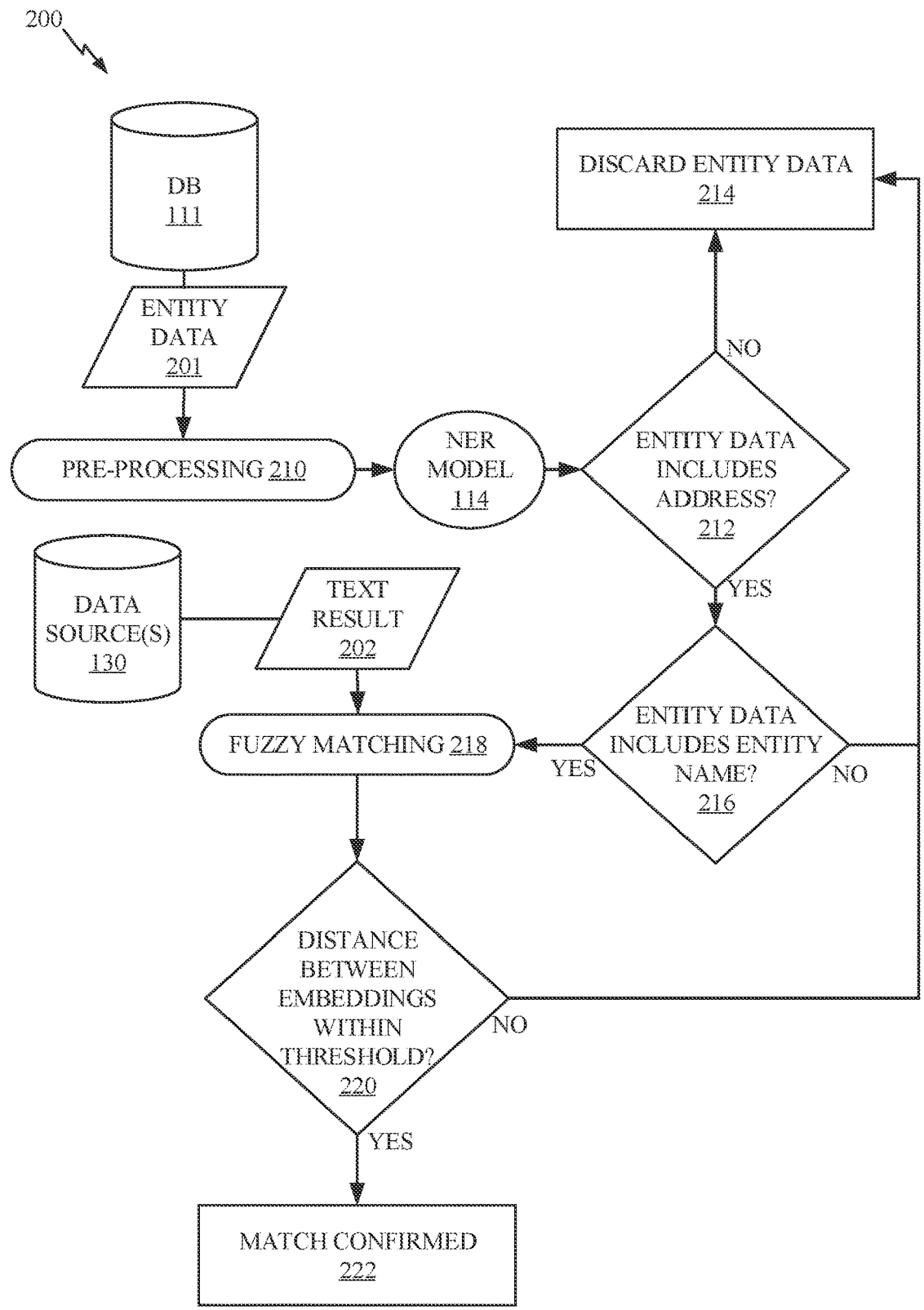
FIG. 2 depicts an example of matching text results to an entity for automated health scoring through meta-learning.

FIG. 2 is an illustration 200 of matching text results to an entity for automated health scoring through meta-learning. Illustration 200 includes DB 111, data source(s) 130, and NER Model 114 of FIG. 1, and may correspond to operations performed by scoring engine 112 of FIG. 1.

Entity data 201 is retrieved from DB 111 and may undergo pre-processing 210. For example, pre-processing 210 may include removing extra characters and symbols such as #( ),%;_:<>{ }, removing entity data with empty addresses, correcting typographical errors, utilizing rules such as regular expressions to eliminate easy-to-identify non-address text, and/or the like.

After pre-processing 210, the pre-processed entity data is used to provide one or more inputs to NER model 114. As described in more detail above, NER model 114 may be based on a pre-trained BERT model that has been fine-tuned for address extraction. In one example, NER model 114 is trained using Jaccardian distance (similarity coefficient) in order to determine whether input text includes a physical address and, if so, extract the physical address. Jaccardian distance involves measuring the dissimilarity between data sets, and is obtained by subtracting the Jaccard similarity coefficient from 1.

At decision block 212, it is determined whether the entity data includes an address. If the entity data is determined not to include an address, then the entity data is discarded at block 214. For example, entity data that is discarded may be excluded from further processing related to automated health scoring. If the entity data is determined to include an address, the process continues at decision block 216, where it is determined whether the entity data includes an entity name (e.g., whether any text was entered into a name field. If the entity data is determined not to include a name, then the entity data is discarded at block 214. If the entity data is determined to include a name, then the process may continue with fuzzy matching 218.

In one example, fuzzy matching 218 involves providing the address and the name from the entity data to a fuzzy matching component, such as fuzzy matching engine 140 of FIG. 1, which may return one or more text results (e.g., text result 202 from data source(s) 130) are a match for the entity name and address (if any such text results are found). In certain embodiments, a result of fuzzy matching 218, such as a potentially matching text result 202, is confirmed based on comparing an embedding of the name from the entity data with an embedding of the text that may or may not be a match for the entity name. For example, an embedding model (e.g., a BERT model or other type of embedding model) may be used to generate the embeddings, and the embeddings may be compared using a similarity measure such as cosine distance (e.g., cosine similarity). At decision block 220, it is determined whether the distance between the embeddings is within a threshold. If the distance between the embeddings is not within a threshold, then the text result 202 is discarded at block 214. If the distance between the embeddings is within the threshold, then a match is confirmed at block 222. When a match is confirmed, the text result 202 may be determined to be a match for the entity, meaning that it contains an address and a name of the entity, and will be used in further processing related to automated health scoring as described herein.

It is noted that certain aspects of the techniques described herein are optional and may potentially be omitted. For example, use of fuzzy matching may be omitted, comparison of embeddings may be omitted, applying rules and/or regular expressions may be omitted, and/or the like.

Example of Automated Health Scoring Through Meta-Learning

Figure 3:
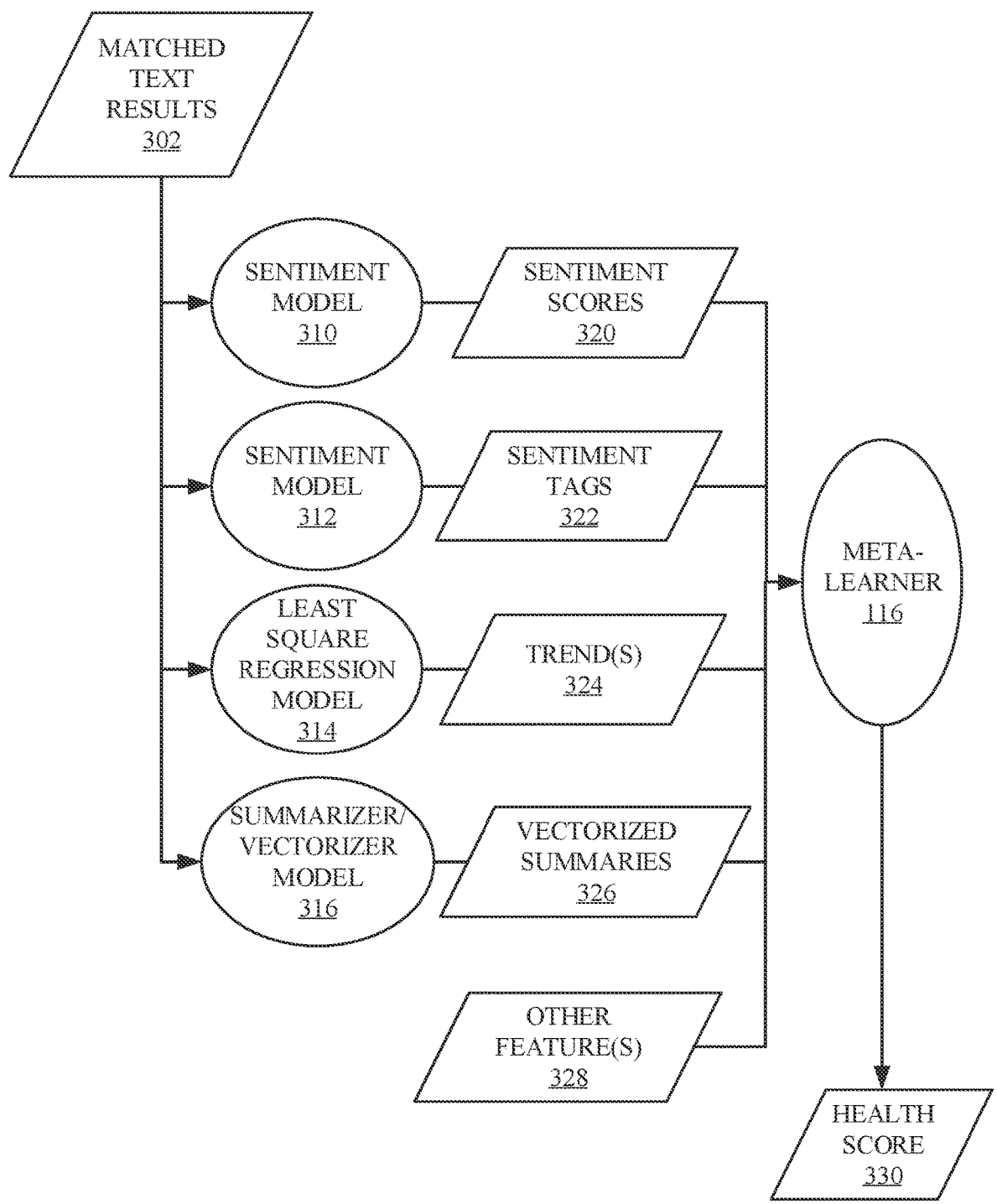
FIG. 3 depicts an example of automated health scoring through meta-learning.

FIG. 3 is an illustration 300 of an example of automated health scoring through meta-learning. Illustration 300 includes meta-learner 116 of FIG. 1, and may relate to operations performed by scoring engine 112 of FIG. 1.

Matched text results 302 represent text results that have been matched to an entity, such as using techniques described above with respect to FIG. 2. For example, matched text results 302 may be text results that have been determined to include an address and a name of the entity.

Matched text results 302 are used to provide one or more inputs to sentiment model 310, sentiment model 312, least square regression model 314, and summarizer/vectorizer model 316, all of which may be examples of models 115 of FIG. 1. For example, while depicted separately from meta-learner 116, all of these models may be part of an ensemble of models included within meta-learner 116.

Sentiment model 310 and/or sentiment model 312 may be machine learning models that have been trained to output indications of sentiment present in text inputs. For example, sentiment model 310 may be trained to output sentiment scores 320 (e.g., numerical values indicating an extent to which text input includes positive sentiment) and sentiment model 312 may be trained to output sentiment tags 322 (e.g., indications of which sentiments are present in text input, such as positive sentiment or negative sentiment, and/or specific sentiments such as anger, confusion, concern, happiness, confidence, and/or the like). In one example, sentiment model 310 and/or sentiment model 312 is a Robustly Optimized BERT Pretraining Approach (RoBERTa) model.

Least square regression model 314 is an example of a model that outputs trend(s) 324 based on a series of input texts. The least squares method generally refers to a statistical procedure for finding the best fit for a set of data points by minimizing the sum of the offsets or residuals of points from the plotted curve. A trend 324 may indicate, for example, that reviews of a business have become more negative or more positive over time and/or after a certain point. In another example, a trend 324 may indicate that reviews of a business became significantly more rare or stopped altogether after a certain point.

Summarizer/vectorizer model 316 generally represents one or more machine learning models that have been trained to output a summary of an input text and/or a vector representation (e.g., including one or more embeddings) of the input text and/or the summary of the input text, such as vectorized summaries 326. Summarizer/vectorizer model 316 may, for example, comprise a BERT model. In some embodiments, summarizer/vectorizer model 316 may comprise a denoising autoencoder, and/or may use a standard transformer-based neural machine translation architecture. In one example, summarizer/vectorizer model 316 comprises a bidirectional auto-regressive transformer (BART) model. Each vectorized summary 326 may, for example, comprise one or more embeddings representing a summary (e.g., shortened textual summary) of a given matched text result 302.

One or more other features 328 may also be used for automated health scoring. For example, other features 328 of an entity may include known attributes of the entity such as business type, amount of time a business has been in existence, size of a business (e.g., number of employees, amount of annual revenue, and/or the like), other business known to be affiliated with a business, and/or the like. For example, other feature(s) 328 may include one or more attributes of an entity that relate to a reputation or health of the entity. In some embodiments, other features 328 include additional features identified based on matched text results 302, such as ratings (e.g., star, numerical, or categorical ratings provided by users in association with text reviews), number of reviews, number of positive review, number of negative reviews, and/or the like. In some embodiments, other features 328 include the address of the entity (e.g., identified using NER model 114 of FIG. 1), which may cleaned up through post-processing, such as using rules and/or regular expressions.

Meta-learner 116 processes sentiment scores 320, sentiment tags 322, trend(s) 324, vectorized summaries 326, and/or other feature(s) 328 in order to determine a health score 330 for the entity. Health score 330 may be output by meta-learner 116, and may be a numerical value (e.g., between 0 and 1) that indicates a likelihood that the entity has an overall positive health status. It is noted that other types of health scores are possible.

In some embodiments, a segmented approach is utilized in which a first model (e.g., meta-learner 116) is used to determine health scores for companies that have available online information (e.g., text results) and another model is used for companies that do not have available online information. For example, the other model that is used for companies that do not have available online information may be a conventional health scoring model that is based on data known to the software application to be associated with the entity without reliance on online information and/or certain other techniques described herein.

Improved Targeted Content Based on Improved Automated Health Scoring

Figure 4:
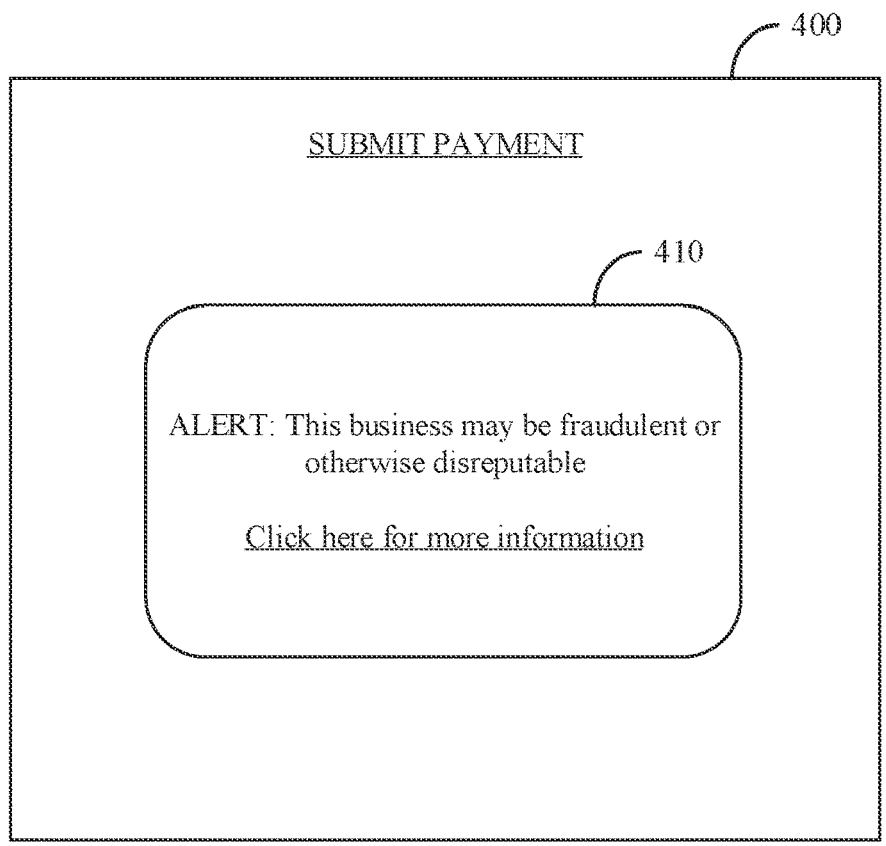
FIG. 4 depicts an example of providing targeted content via a software application based on automated health scoring through meta-learning.

FIG. 4 illustrates an example user interface screen 400 for providing improved targeted content based on improved automated health scoring techniques described herein. For example, user interface screen 400 may correspond to client application 122 of FIG. 1.

User interface screen 400 represents a screen of a graphical user interface associated with a financial services application. For example, a user may interact with user interface screen 400 to submit payment to a business for one or more goods or services.

An alert 410 is displayed within user interface screen 400, indicating that the business to which the payment corresponds may be fraudulent or otherwise disreputable, including a link that, when selected, causes additional information related to alert 410 to be displayed (e.g., including the determined health score for the business and/or indicating one or more factors that contributed to a low health score for the business, which may be determined based on meta-learner 116 of FIGS. 1 and 3). Alert 410 may correspond to content 118 of FIG. 1, and may be generated by server 110 of FIG. 1, such as based on an a health score determined using techniques described herein.

It is noted that user interface screen 400 and alert 410 are included as an example, and other methods of providing content to users may be employed without departing from the scope of the present disclosure. For example, content may be provided to a user via email, text message, phone call, advertisement, social media, and/or the like.

Furthermore, while certain embodiments are described with respect to financial software applications, techniques described herein may also be utilized to provide other types of targeted content to users based on health scores, such as offers of goods and/or services, discount offers, recommendations of actions to perform, advertisements, and/or the like. In some embodiments, health scores determines using techniques described herein may be used to determine whether to offer a loan, line of credit, and/or other financial product to an entity, what terms (e.g., pricing) should be offered for such a loan, line of credit, and/or other financial product, and/or the like. For example, the health score may be used as part of a capital risk or credit risk model that is used to determine risk associated with offering a loan, line of credit, and/or other financial product to an entity. In another example, the health score may be used to monitor business health for companies using payroll service, such as to adjust payroll processing limits. In still further examples, the health score may be used to monitor for anomalous behavior of companies enrolled in a payment service in order to control exposure to write off loss or may be used in general financial risk assessment, such as when onboarding small or medium sized business to money movement products.

Example Operations for Automated Health Scoring Through Meta-Learning

Figure 5:
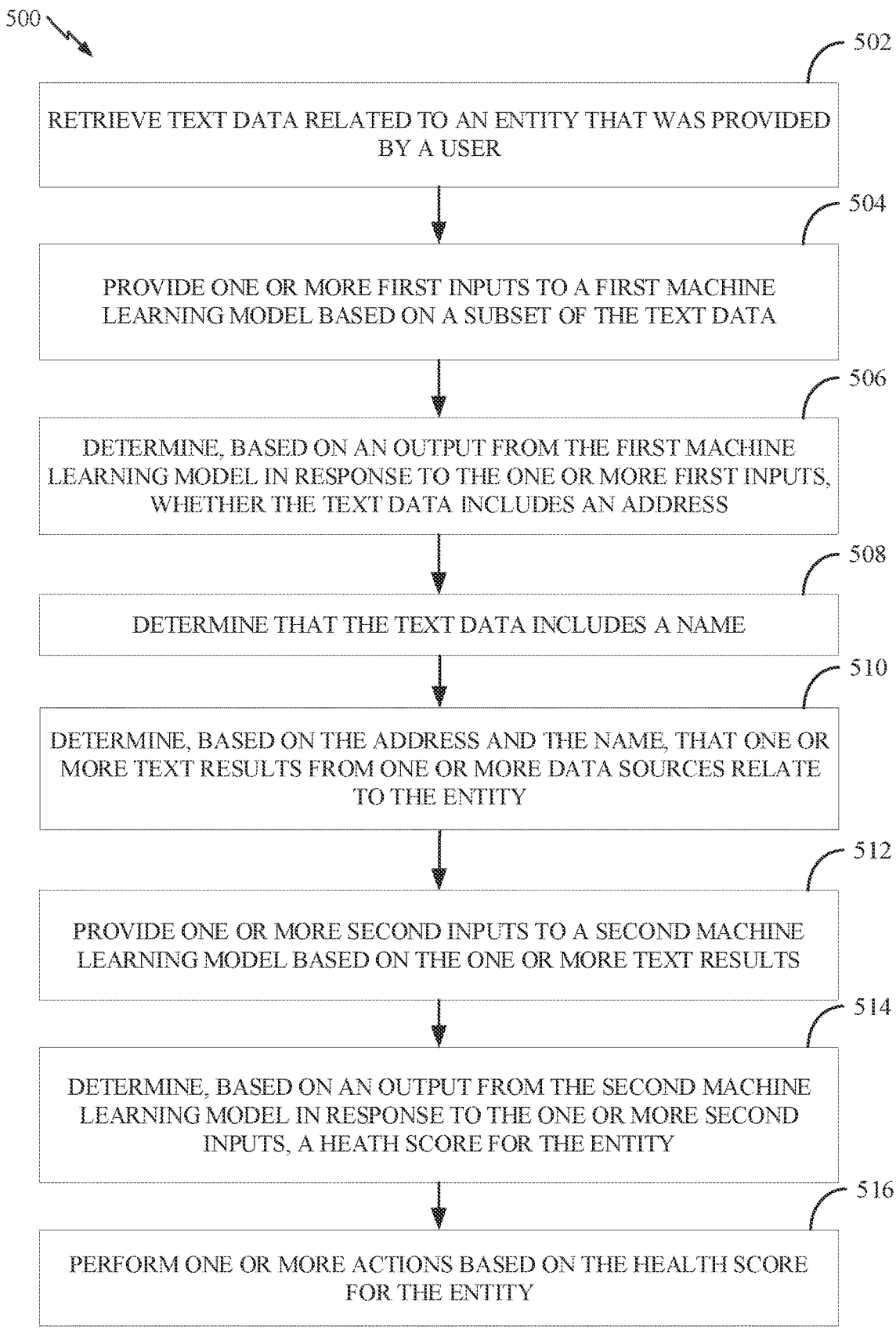
FIG. 5 depicts example operations related to automated health scoring through meta-learning.

FIG. 5 depicts example operations 500 for automated health scoring through meta-learning. For example, operations 500 may be performed by server 110 of FIG. 1.

Operations 500 begin at step 502, retrieving text data related to an entity that was provided by a user.

Operations 500 continue at step 504, with providing one or more first inputs to a first machine learning model based on a subset of the text data.

In some embodiments, the first machine learning model has been trained through a supervised learning process based on historical text inputs associated with labels indicating whether the historical text inputs include address information.

Operations 500 continue at step 506, with determining, based on an output from the first machine learning model in response to the one or more first inputs, whether the text data includes an address.

Operations 500 continue at step 508, with determining that the text data includes a name.

Operations 500 continue at step 510, with determining, based on the address and the name, that one or more text results from one or more data sources relate to the entity.

In some embodiments, the determining that the one or more text results from the one or more data sources relate to the entity comprises searching one or more publicly available data sources based on the address and the name. For example, the determining that the one or more text results from the one or more data sources relate to the entity may be based on fuzzy matching. Certain embodiments further comprise confirming the fuzzy matching based on comparing embeddings.

Operations 500 continue at step 506, with providing one or more second inputs to a second machine learning model based on the one or more text results. In some embodiments, the second machine learning model comprises an ensemble of a plurality of machine learning models that have been trained based on a training data set comprising features of entities associated with labels indicating whether the entities are healthy. For example, the features of the entities in the training data used to train the second machine learning model may comprise one or more features related to respective text results matched to the entities.

In some embodiments, the providing of the one or more second inputs to the second machine learning model is based further on determining a sentiment of each given text result in the subset of the set of text results. For example, the sentiment of each given text result in the subset of the set of text results may be determined through the use of a trained sentiment model.

In certain embodiments, providing of the one or more second inputs to the second machine learning model is based further on determining a trend related to two or more text results in the subset of the set of text results. In some embodiments, the providing of the one or more second inputs to the second machine learning model is based further on determining vector representations of each given text result in the subset of the set of text results.

Operations 500 continue at step 508, with determining, based on an output from the second machine learning model in response to the one or more second inputs, a heath score for the entity.

Operations 500 continue at step 510, with performing one or more actions based on the health score for the entity. In certain embodiments, the performing of the one or more actions based on the health score for the entity comprises automatically selecting content to provide to a user based on the health score for the entity. For example, the content may be provided to a user via a user interface.

Some embodiments further comprise re-training the second machine learning model based on user feedback with respect to the health score for the entity.

Notably, method 500 is just one example with a selection of example steps, but additional methods with more, fewer, and/or different steps are possible based on the disclosure herein.

Example Computing Systems

Figure 6A:
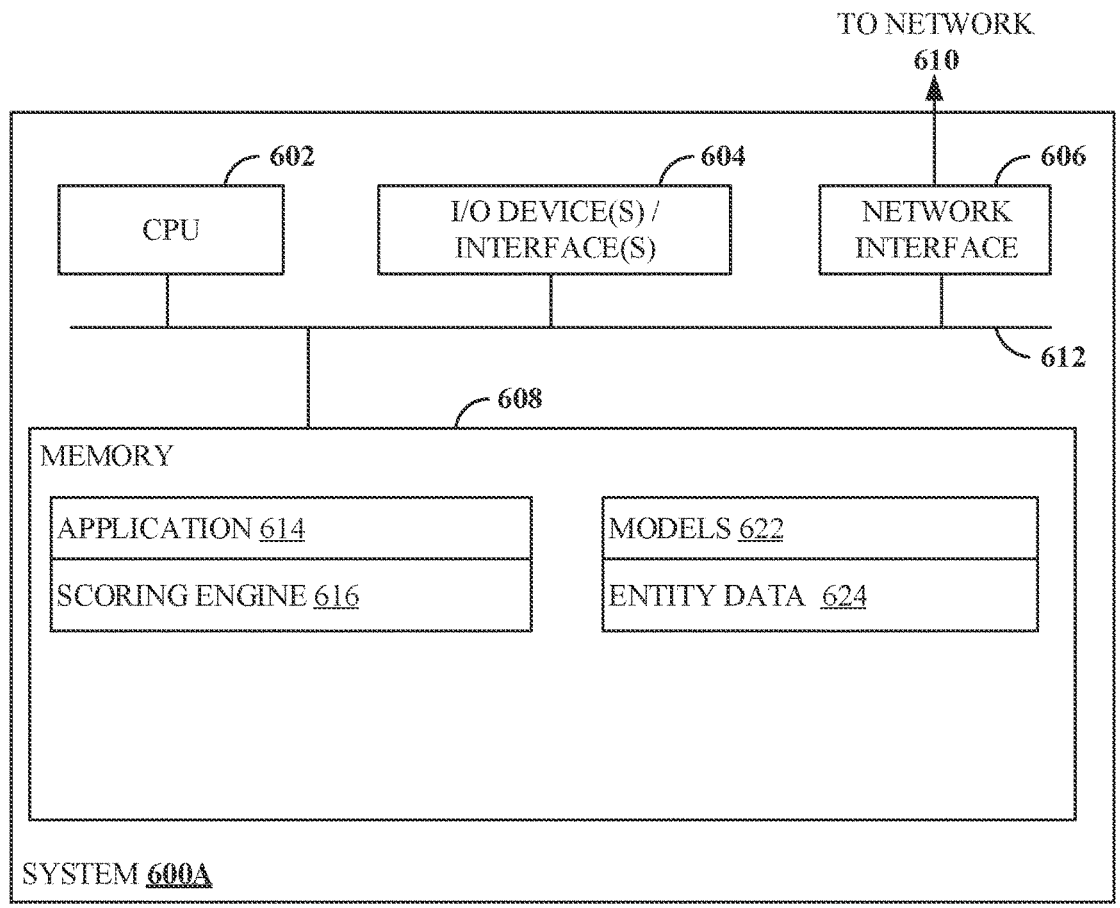
FIGS. 6A and 6B depict example processing systems related to automated health scoring through meta-learning.

FIG. 6A illustrates an example system 600 with which embodiments of the present disclosure may be implemented. For example, system 600A may correspond to server 110 of FIG. 1, and may be configured to perform one or more of operations 500 of FIG. 5.

System 600A includes a central processing unit (CPU) 602, one or more I/O device interfaces 604 that may allow for the connection of various I/O devices 614 (e.g., keyboards, displays, mouse devices, pen input, etc.) to the system 600A, network interface 606, a memory 608, and an interconnect 612. It is contemplated that one or more components of system 600A may be located remotely and accessed via a network 610. It is further contemplated that one or more components of system 600A may comprise physical components or virtualized components.

CPU 602 may retrieve and execute programming instructions stored in the memory 608. Similarly, the CPU 602 may retrieve and store application data residing in the memory 608. The interconnect 612 transmits programming instructions and application data, among the CPU 602, I/O device interface 604, network interface 606, and memory 608. CPU 602 is included to be representative of a single CPU, multiple CPUs, a single CPU having multiple processing cores, and other arrangements.

Additionally, the memory 608 is included to be representative of a random access memory or the like. In some embodiments, memory 608 may comprise a disk drive, solid state drive, or a collection of storage devices distributed across multiple storage systems. Although shown as a single unit, the memory 608 may be a combination of fixed and/or removable storage devices, such as fixed disc drives, removable memory cards or optical storage, network attached storage (NAS), or a storage area-network (SAN).

Figure 6B:
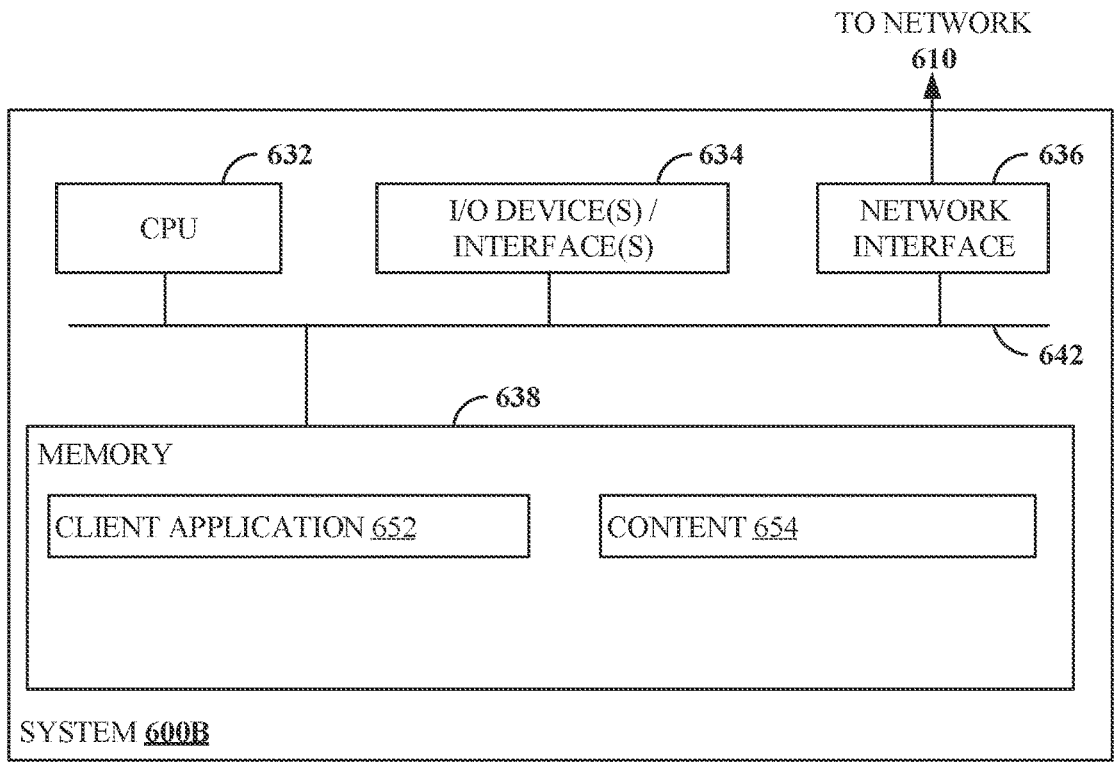

As shown, memory 608 includes an application 614, which may be a software application that performs one or more actions based on automated health scoring of an entity according to techniques described herein, such as sending content from a serve-side application 614 to client-side applications on client devices (e.g., client application 654 on system 600B of FIG. 6B). Memory 608 further includes scoring engine 616, which may correspond to scoring engine 112 of FIG. 1.

Memory 608 further comprises models 622, which may include NER model 114, model(s) 115, and/or meta-learner 116 of FIG. 1. Memory 608 further comprises entity data 624, which may include data related to entities for which automated scoring is performed, such as entity data 201 and/or text results 202 of FIG. 2, matched text results 302 and other features 328 of FIG. 3, and/or other data related to entities. Entity data 624 may also include health scores determined for entities, such as health score 330 of FIG. 3.

FIG. 6B illustrates another example system 600B with which embodiments of the present disclosure may be implemented. For example, system 600B may correspond to client 120 of FIG. 1, and may be configured to display user interface screen 400 of FIG. 4.

System 600B includes a CPU 632, one or more I/O device interfaces 634 that may allow for the connection of various I/O devices 634 (e.g., keyboards, displays, mouse devices, pen input, etc.) to the system 600B, network interface 636, a memory 638, and an interconnect 642. It is contemplated that one or more components of system 600B may be located remotely and accessed via a network 610. It is further contemplated that one or more components of system 600B may comprise physical components or virtualized components.

CPU 632 may retrieve and execute programming instructions stored in the memory 638. Similarly, the CPU 632 may retrieve and store application data residing in the memory 638. The interconnect 642 transmits programming instructions and application data, among the CPU 632, I/O device interface 634, network interface 636, and memory 638. CPU 632 is included to be representative of a single CPU, multiple CPUs, a single CPU having multiple processing cores, and other arrangements.

Additionally, the memory 638 is included to be representative of a random access memory or the like. In some embodiments, memory 638 may comprise a disk drive, solid state drive, or a collection of storage devices distributed across multiple storage systems. Although shown as a single unit, the memory 638 may be a combination of fixed and/or removable storage devices, such as fixed disc drives, removable memory cards or optical storage, network attached storage (NAS), or a storage area-network (SAN).

As shown, memory 638 includes a client application 652, which may correspond to client application 122 of FIG. 1, and content 654, which may include content 118 of FIG. 1 and/or alert 410 of FIG. 4. For example, content 118 may be displayed within a user interface associated with client application 652, such as in a manner like that described above with respect to FIG. 4.

Example Clauses

Clause 1: A method for automated health scoring through meta-learning, comprising: retrieving text data related to an entity that was provided by a user; providing one or more first inputs to a first machine learning model based on a subset of the text data; determining, based on an output from the first machine learning model in response to the one or more first inputs, whether the text data includes an address; determining that the text data includes a name; determining, based on the address and the name, that one or more text results from one or more data sources relate to the entity; providing one or more second inputs to a second machine learning model based on the one or more text results; determining, based on an output from the second machine learning model in response to the one or more second inputs, a health score for the entity; and performing one or more actions based on the health score for the entity.

Clause 2: The method of Clause 1, wherein the determining that the one or more text results from the one or more data sources relate to the entity comprises searching one or more publicly available data sources based on the address and the name.

Clause 3: The method of any one of Clause 1-2, wherein the first machine learning model has been trained through a supervised learning process based on historical text inputs associated with labels indicating whether the historical text inputs include address information.

Clause 4: The method of any one of Clause 1-3, wherein the second machine learning model comprises an ensemble of a plurality of machine learning models that have been trained based on a training data set comprising features of entities associated with labels indicating whether the entities are healthy.

Clause 5: The method of Clause 4, wherein the features of the entities in the training data used to train the second machine learning model comprise one or more features related to respective text results matched to the entities.

Clause 6: The method of any one of Clause 1-5, wherein the providing of the one or more second inputs to the second machine learning model is based further on determining a sentiment of each given text result in the one or more text results.

Clause 7: The method of Clause 6, wherein the sentiment of each given text result in the one or more text results is determined through the use of a trained sentiment model.

Clause 8: The method of any one of Clause 1-7, wherein the providing of the one or more second inputs to the second machine learning model is based further on determining a trend related to two or more text results in the one or more text results.

Clause 9: The method of any one of Clause 1-8, wherein the providing of the one or more second inputs to the second machine learning model is based further on determining vector representations of each given text result in the one or more text results.

Clause 10: The method of any one of Clause 1-9, wherein the determining that the one or more text results from the one or more data sources relate to the entity is based on fuzzy matching.

Clause 11: The method of Clause 10, further comprising confirming the fuzzy matching based on comparing embeddings.

Clause 12: The method of any one of Clause 1-10, further comprising re-training the second machine learning model based on user feedback with respect to the health score for the entity.

Clause 13: The method of any one of Clause 1-12, wherein the performing of the one or more actions based on the health score for the entity comprises automatically selecting content to provide to a user based on the health score for the entity.

Clause 14: A system for automated health scoring through meta-learning, comprising: one or more processors; and a memory comprising instructions that, when executed by the one or more processors, cause the system to: retrieve text data related to an entity that was provided by a user; provide one or more first inputs to a first machine learning model based on a subset of the text data; determine, based on an output from the first machine learning model in response to the one or more first inputs, whether the text data includes an address; determine that the text data includes a name; determining, based on the address and the name, that one or more text results from one or more data sources relate to the entity; provide one or more second inputs to a second machine learning model based on the one or more text results; determine, based on an output from the second machine learning model in response to the one or more second inputs, a health score for the entity; and perform one or more actions based on the health score for the entity.

Clause 15: The system of Clause 14, wherein the determining that the one or more text results from the one or more data sources relate to the entity comprises searching one or more publicly available data sources based on the address and the name.

Clause 16: The system of any one of Clause 14-15, wherein the first machine learning model has been trained through a supervised learning process based on historical text inputs associated with labels indicating whether the historical text inputs include address information.

Clause 17: The system of any one of Clause 14-16, wherein the second machine learning model comprises an ensemble of a plurality of machine learning models that have been trained based on a training data set comprising features of entities associated with labels indicating whether the entities are healthy.

Clause 18: The system of Clause 17, wherein the features of the entities in the training data used to train the second machine learning model comprise one or more features related to respective text results matched to the entities.

Clause 19: The system of any one of Clause 14-18, wherein the providing of the one or more second inputs to the second machine learning model is based further on determining a sentiment of each given text result in the one or more text results.

Clause 20: A non-transitory computer-readable medium comprising instructions that, when executed by one or more processors of a computing system, cause the computing system to: retrieve text data related to an entity that was provided by a user; provide one or more first inputs to a first machine learning model based on a subset of the text data; determine, based on an output from the first machine learning model in response to the one or more first inputs, whether the text data includes an address; determine that the text data includes a name; determining, based on the address and the name, that one or more text results from one or more data sources relate to the entity; provide one or more second inputs to a second machine learning model based on the one or more text results; determine, based on an output from the second machine learning model in response to the one or more second inputs, a health score for the entity; and perform one or more actions based on the health score for the entity.

Additional Considerations

The preceding description provides examples, and is not limiting of the scope, applicability, or embodiments set forth in the claims. Changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

The preceding description is provided to enable any person skilled in the art to practice the various embodiments described herein. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and other operations. Also, "determining" may include receiving (e.g., receiving information), accessing (e.g., accessing data in a memory) and other operations. Also, "determining" may include resolving, selecting, choosing, establishing and other operations.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and other types of circuits, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method for automated health scoring through meta-learning, comprising:
    retrieving text data related to an entity that was provided by a user;
    providing one or more first inputs to a first machine learning model based on a subset of the text data;
    determining, based on an output from the first machine learning model in response to the one or more first inputs, that a first portion of the subset of the text data includes an address and a name;
    discarding a second portion of the subset of the text data that does not include the address or the name;
    determining, based on the address and the name, that one or more text results from one or more data sources relate to the entity;
    providing one or more second inputs to a second machine learning model based on the one or more text results and based further on determining vector representations of each given text result in the one or more text results;
    determining, based on an output from the second machine learning model in response to the one or more second inputs, a health score for the entity;
    performing one or more actions based on the health score for the entity; and
    receiving user feedback with respect to the health score determined for the entity, wherein the second machine learning model is re-trained based on the user feedback.

2. The method of claim 1, wherein the determining that the one or more text results from the one or more data sources relate to the entity comprises searching one or more publicly available data sources based on the address and the name.

3. The method of claim 1, wherein the first machine learning model has been trained through a supervised learning process based on historical text inputs associated with labels indicating whether the historical text inputs include address information.

4. The method of claim 1, wherein the second machine learning model comprises an ensemble of a plurality of machine learning models that have been trained based on a training data set comprising features of entities associated with labels indicating whether the entities are healthy.

5. The method of claim 4, wherein the features of the entities in the training data used to train the second machine learning model comprise one or more features related to respective text results matched to the entities.

6. The method of claim 1, wherein the providing of the one or more second inputs to the second machine learning model is based further on determining a sentiment of each given text result in the one or more text results.

7. The method of claim 6, wherein the sentiment of each given text result in the one or more text results is determined through the use of a trained sentiment model.

8. The method of claim 1, wherein the providing of the one or more second inputs to the second machine learning model is based further on determining a trend related to two or more text results in the one or more text results.

9. The method of claim 1, wherein the determining that the one or more text results from the one or more data sources relate to the entity is based on fuzzy matching.

10. The method of claim 9, further comprising confirming the fuzzy matching based on comparing embeddings.

11. The method of claim 1, wherein the performing of the one or more actions based on the health score for the entity comprises automatically selecting content to provide to a user based on the health score for the entity.

12. The method of claim 1, wherein the determining that the text data includes the name is in response to the determining, based on the output from the first machine learning model in response to the one or more first inputs, the text data includes the address.

13. A system for automated health scoring through meta-learning, comprising:
one or more processors; and
a memory comprising instructions that, when executed by the one or more processors, cause the system to:
retrieve text data related to an entity that was provided by a user;
provide one or more first inputs to a first machine learning model based on a subset of the text data;
determine, based on an output from the first machine learning model in response to the one or more first inputs, that a first portion of the subset of the text data includes an address and a name;
discard a second portion of the subset of the text data that does not include the address or the name;
determine, based on the address and the name, that one or more text results from one or more data sources relate to the entity;
provide one or more second inputs to a second machine learning model based on the one or more text results;
determine, based on an output from the second machine learning model in response to the one or more second inputs, a health score for the entity;
perform one or more actions based on the health score for the entity; and
receive user feedback with respect to the health score determined for the entity, wherein the second machine learning model is re-trained based on the user feedback.

14. The system of claim 13, wherein the determining that the one or more text results from the one or more data sources relate to the entity comprises searching one or more publicly available data sources based on the address and the name.

15. The system of claim 13, wherein the first machine learning model has been trained through a supervised learning process based on historical text inputs associated with labels indicating whether the historical text inputs include address information.

16. The system of claim 13, wherein the second machine learning model comprises an ensemble of a plurality of machine learning models that have been trained based on a training data set comprising features of entities associated with labels indicating whether the entities are healthy.

17. The system of claim 16, wherein the features of the entities in the training data used to train the second machine learning model comprise one or more features related to respective text results matched to the entities.

18. The system of claim 13, wherein the providing of the one or more second inputs to the second machine learning model is based further on determining a sentiment of each given text result in the one or more text results.

19. A non-transitory computer-readable medium comprising instructions that, when executed by one or more processors of a computing system, cause the computing system to:
retrieve text data related to an entity that was provided by a user;
provide one or more first inputs to a first machine learning model based on a subset of the text data;
determine, based on an output from the first machine learning model in response to the one or more first inputs, that a first portion of the subset of the text data includes an address and a name;
discard a second portion of the subset of the text data that does not include the address or the name;
determine, based on the address and the name, that one or more text results from one or more data sources relate to the entity;
provide one or more second inputs to a second machine learning model based on the one or more text results;
determine, based on an output from the second machine learning model in response to the one or more second inputs, a health score for the entity;
perform one or more actions based on the health score for the entity; and
receive user feedback with respect to the health score determined for the entity, wherein the second machine learning model is re-trained based on the user feedback.

* * * * *